United States Patent
Cui et al.

(10) Patent No.: US 8,217,057 B2
(45) Date of Patent: Jul. 10, 2012

(54) POLYMORPHS OF A C-MET/HGFR INHIBITOR

(75) Inventors: Jingrong Jean Cui, San Diego, CA (US); Michelle Bich Tran-Dubé, San Diego, CA (US)

(73) Assignee: Pfizer Inc., New York, NY (US)

(*) Notice: Subject to any disclaimer, the term of this patent is extended or adjusted under 35 U.S.C. 154(b) by 1079 days.

(21) Appl. No.: 12/095,116

(22) PCT Filed: Nov. 23, 2006

(86) PCT No.: PCT/IB2006/003383
§ 371 (c)(1),
(2), (4) Date: May 27, 2008

(87) PCT Pub. No.: WO2007/066185
PCT Pub. Date: Jun. 14, 2007

(65) Prior Publication Data
US 2008/0293769 A1      Nov. 27, 2008

Related U.S. Application Data

(60) Provisional application No. 60/742,676, filed on Dec. 5, 2005.

(51) Int. Cl.
*A61K 31/445* (2006.01)
*C07D 401/04* (2006.01)

(52) U.S. Cl. ........................ 514/318; 546/193
(58) Field of Classification Search .................. 514/318; 546/193
See application file for complete search history.

(56) References Cited

U.S. PATENT DOCUMENTS

| | | |
|---|---|---|
| 6,313,137 B1 | 11/2001 | Amin et al. |
| 6,498,165 B1 | 12/2002 | Armstrong et al. |
| 6,825,198 B2 | 11/2004 | Chiang et al. |
| 6,992,087 B2 | 1/2006 | Verhoest et al. |
| 6,995,161 B2 | 2/2006 | Yoon et al. |
| 7,205,408 B2 | 4/2007 | Davies et al. |
| 7,230,098 B2 | 6/2007 | Cui et al. |
| 7,858,643 B2 * | 12/2010 | Cui et al. .................. 514/318 |
| 2006/0046991 A1 | 3/2006 | Cui et al. |
| 2006/0128724 A1* | 6/2006 | Cui et al. ............... 514/255.05 |
| 2006/0178374 A1 | 8/2006 | Cui et al. |
| 2007/0072874 A1 | 3/2007 | Cui et al. |

FOREIGN PATENT DOCUMENTS

EP         0 204 285       1/1992
(Continued)

OTHER PUBLICATIONS

Berstein :Polymorphism in mole . . . p. 46 (2002.*
(Continued)

*Primary Examiner* — Celia Chang
(74) *Attorney, Agent, or Firm* — Stephen D. Prodnuk; Vincent P. Liptak

(57) ABSTRACT

This invention relates to polymorphs of (R)-3-[1-(2,6-Dichloro-3-fluoro-phenyl)-ethoxy]-5-(1-piperidin-4-yl-1H-pyrazol-4-yl)-pyridin-2-ylamine that are useful in the treatment of abnormal cell growth, such as cancer, in mammals. This invention also relates to compositions including such salts and polymorphs, and to methods of using such compositions in the treatment of abnormal cell growth in mammals, especially humans.

10 Claims, 2 Drawing Sheets

FOREIGN PATENT DOCUMENTS

| | | |
|---|---|---|
| EP | 1 044 967 | 8/2004 |
| JP | 7 109260 | 4/1995 |
| WO | WO 93/15055 | 8/1993 |
| WO | WO 98/37080 | 8/1998 |
| WO | WO 99/55706 | 11/1999 |

OTHER PUBLICATIONS

Borchardt et al. "Pharmaceutical profil . . . " p. 93-125 (2004).*

Byrn et al. "Solid state . . . " p. 63 (1999).*

Dean "Analytical Chem . . . "p. 10.24-10.26 (1993).*

Bradbury H., et al., "New Non-Peptide Endothelin-A Receptor Antagonists: Synthesis, Biological Properties, and Structure-Activity Relationships of 5-(Dimethylamino)-N-pyridyl-, -N-pyrimidinyl-, -N-pyridazinyl-, and -N-pyrazinyl-1-naphthalenesulfonamides," *Journal of Medicinal Chemistry*, 1997, 996-1004, vol. 40, No. 6.

Bristol, J., et al., "An Improved Synthesis of 2-Amino-3-alkyloxypyridines by a Phase-Transfer Catalyzed Ether Synthesis," *Synthesis*, 1981, 971-973, vol. 12.

Dennin, F., et al., "Synthesis of Derivatives of Pyrazino[1,2-α]pyrimidin-4-ones," *Journal of Heterocyclic Chemistry*, 1990, 1639-1643, vol. 27.

Foks, H., et al, "Studies on Pyrazine Derivatives. XXX. Synthesis of Pyrazinylamino-1,3-Diazacycloalkanes of Potential Circulatory Activity," *Acta Poloniae Pharmaceutica*, 1997, 55-62, vol. 54, No. 1.

Gavezzotti, A., "Are Crystal Structures Predictable?," *Accounts of Chemical Research*, 1994, 309-314, vol. 27, No. 10.

Hanahan, D., et al., "The Hallmarks of Cancer," *Cell*, 2000, 57-70, vol. 100.

Kaminski, J., et al., "Antiulcer Agents. 2. Gastric Antisecretory, Cytoprotective, and Metabolic Properties of Substituted Imidazo[1,2-a]pyridines and Analogues," *Journal of Medicinal Chemistry*, 1987, 2031-2046, vol. 30, No. 11.

Shimomura, O., et al., "Semi-synthetic aequorins with improved sensitivity to Ca2+ions," *Biochemical Journal*, 1989, 913-920, vol. 261.

Sollogoub, M., et al., "First synthesis of 1-deazacytidine, the C-nucleoside analogue of Cytidine," *Tetrahedron Letters*, 2002, 3121-3123, vol. 43.

Vippagunta, S., et al., "Crystalline Solids," *Advanced Drug Delivery Reviews*, 2001, 3-26, vol. 48.

* cited by examiner

POLYMORPHS OF A C-MET/HGFR INHIBITOR

This application is a 371 application of PCT/IB2006/003383, filed on Nov. 23, 2006, which claims the benefit of U.S. Provisional Application No. 60/742,676 filed on Dec. 5, 2005, the contents of which is hereby incorporated by reference in their entireties.

FIELD OF THE INVENTION

This invention relates to polymorphs of (R)-3-[1-(2,6-Dichloro-3-fluoro-phenyl)-ethoxy]-5-(1-piperidin-4-yl-1H-pyrazol-4-yl)-pyridin-2-ylamine that are useful in the treatment of abnormal cell growth, such as cancer, in mammals. This invention also relates to compositions including such salts and polymorphs, and to methods of using such compositions in the treatment of abnormal cell growth in mammals, especially humans.

BACKGROUND OF THE INVENTION

The compound (R)-3-[1-(2,6-Dichloro-3-fluoro-phenyl)-ethoxy]-5-(1-piperidin-4-yl-1H-pyrazol-4-yl)-pyridin-2-ylamine (also herein referred to as "compound 1") represented by the formula 1

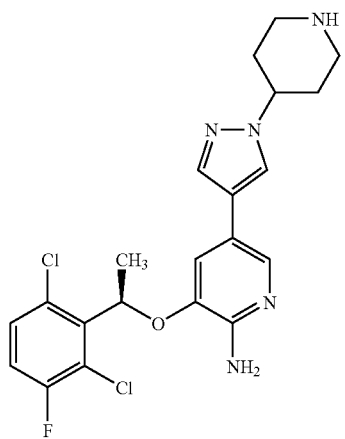

is a potent small-molecule inhibitor of c-Met/HGFR (hepatocyte growth factor receptor) kinase and ALK (anaplastic lymphoma kinase) activity. Compound 1 has anti-tumor properties that are pharmacologically mediated through inhibition of c-Met/HGFR which is involved in the regulation of growth and metastatic progression of a wide variety of tumors types, and ALK which implicated in the pathogenesis of ALCL (anaplastic large cell lymphoma). Compound 1 is disclosed in International Patent Application No. PCT/IB2005/002837 and U.S. patent application Ser. No. 11/212,331, both of which are herein incorporated by reference in their entirety. Additionally, the racemate of compound 1 is disclosed in International Patent Application No. PCT/IB05/002695 and U.S. patent application Ser. No. 11/213,039, both of which are herein incorporated by reference in their entirety.

Human cancers comprise a diverse array of diseases that collectively are one of the leading causes of death in developed countries throughout the world (American Cancer Society, Cancer Facts and Figures 2005. Atlanta: American Cancer Society; 2005). The progression of cancers is caused by a complex series of multiple genetic and molecular events including gene mutations, chromosomal translocations, and karyotypic abnormalities (Hanahan D, Weinberg R A. The hallmarks of cancer. Cell 2000; 100: 57-70). Although the underlying genetic causes of cancer are both diverse and complex, each cancer type has been observed to exhibit common traits and acquired capabilities that facilitate its progression. These acquired capabilities include dysregulated cell growth, sustained ability to recruit blood vessels (i.e., angiogenesis), and ability of tumor cells to spread locally as well as metastasize to secondary organ sites (Hanahan D, Weinberg R A. The hallmarks of cancer. Cell 2000; 100: 57-70). Therefore, the ability to identify novel therapeutic agents that 1) inhibit molecular targets that are altered during cancer progression or 2) target multiple processes that are common to cancer progression in a variety of tumors presents a significant unmet need.

Example 19 of U.S. patent application Ser. No. 11/212,331 describes the preparation of compound 1 which was found to be amorphous. It is advantageous to have polymorphic forms having improved properties, such as improved crystallinity, dissolution properties, and/or decreased hygroscopicity, while maintaining chemical and enantiomeric stability properties.

SUMMARY OF THE INVENTION

In one embodiment, the present invention provides a crystalline form of the free base of (R)-3-[1-(2,6-dichloro-3-fluoro-phenyl)-ethoxy]-5-(1-piperidin-4-yl-1H-pyrazol-4-yl)-pyridin-2-ylamine. In a particular embodiment, the crystalline form of the free base of (R)-3-[1-(2,6-dichloro-3-fluoro-phenyl)-ethoxy]-5-(1-piperidin-4-yl-1H-pyrazol-4-yl)-pyridin-2-ylamine is anhydrous. In another embodiment, the crystalline form of the free base of (R)-3-[1-(2,6-dichloro-3-fluoro-phenyl)-ethoxy]-5-(1-piperidin-4-yl-1H-pyrazol-4-yl)-pyridin-2-ylamine is a hydrate.

In a further aspect the crystalline form is a polymorph form 1 of the free base. In a further aspect, the crystalline form has a powder X-ray diffraction pattern comprising a peak at diffraction angle (2θ) of 19.7±0.1. In a further aspect, the crystalline form has a powder X-ray diffraction pattern comprising peaks at diffraction angles (2θ) of 17.3±0.1 and 19.7±0.1. In a further aspect, the crystalline form has a powder X-ray diffraction pattern comprising peaks at diffraction angles (2θ) of 15.7±0.1, 17.3±0.1, and 19.7±0.1. In a further aspect, the crystalline form has a powder X-ray diffraction pattern comprising peaks at diffraction angles (2θ) of 15.7±0.1, 17.3±0.1, 19.7±0.1, and 26.8±0.1. In a further aspect the crystalline form has a powder X-ray diffraction pattern comprising peaks at diffraction angles (2θ) of 15.7±0.1, 17.3±0.1, 19.7±0.1, 21.0±0.1, and 26.8±0.1. In a further aspect the crystalline form has a powder X-ray diffraction pattern comprising peaks at diffraction angles (2θ) of 15.7±0.1, 17.3±0.1, 19.7±0.1, 21.0±0.1, 21.7±0.1, and 26.8±0.1. In a further aspect the crystalline form has a powder X-ray diffraction pattern comprising peaks at diffraction angles (2θ) of 12.8±0.1, 15.7±0.1, 17.3±0.1, 19.7±0.1, 21.0±0.1, 21.7±0.1, and 26.8±0.1. In a further aspect the crystalline form has a powder X-ray diffraction pattern comprising peaks at diffraction angles (2θ) essentially the same as shown in FIG. 1.

The present invention further provides a pharmaceutical composition comprising the free base polymorph form 1 of compound 1. The present invention further provides a capsule comprising said pharmaceutical composition. In particular aspects of this embodiment, the capsule comprises from 0.1 to 200 mg of the free base polymorph form 1 of compound 1.

In a further aspect the capsule comprises from 25 to 150 mg of the free base polymorph form 1 of compound 1. In a further embodiment, the capsule comprises from 50 to 100 mg of the free base polymorph form 1 of compound 1.

In another embodiment, the invention provides a method of treating cancer in a mammal, including a human, the method comprising administering to the mammal a therapeutically effective amount of a pharmaceutical composition of the present invention.

In another embodiment, the invention provides a method of treating cancer in a mammal, the method comprising administering to the mammal, including a human, a capsule of the present invention.

In one embodiment, the present invention provides a method of treating abnormal cell growth in a mammal, including a human, in need of such treatment comprising, administering to said mammal a therapeutically effective amount of the free base polymorph form 1 of compound 1.

In another embodiment, the abnormal cell growth is mediated by at least one genetically altered tyrosine kinase. In another embodiment, the abnormal cell growth is mediated by hepatocyte growth factor receptor (c-Met/HGFR) kinase or anaplastic lymphoma kinase (ALK). In another embodiment, the abnormal cell growth is mediated by hepatocyte growth factor receptor (c-Met/HGFR) kinase. In another embodiment, the abnormal cell growth is mediated by anaplastic lymphoma kinase (ALK).

In another embodiment, the abnormal cell growth is cancer. In another embodiment, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In yet another embodiment, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

DEFINITIONS

As used herein, unless otherwise indicated, the term "abnormal cell growth" refers to cell growth that is independent of normal regulatory mechanisms (e.g., loss of contact inhibition).

As used herein, unless otherwise indicated, the term "treating" means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" as defined immediately above.

As used herein, the term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.1°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

DETAILED DESCRIPTION OF THE INVENTION

Figure 1:
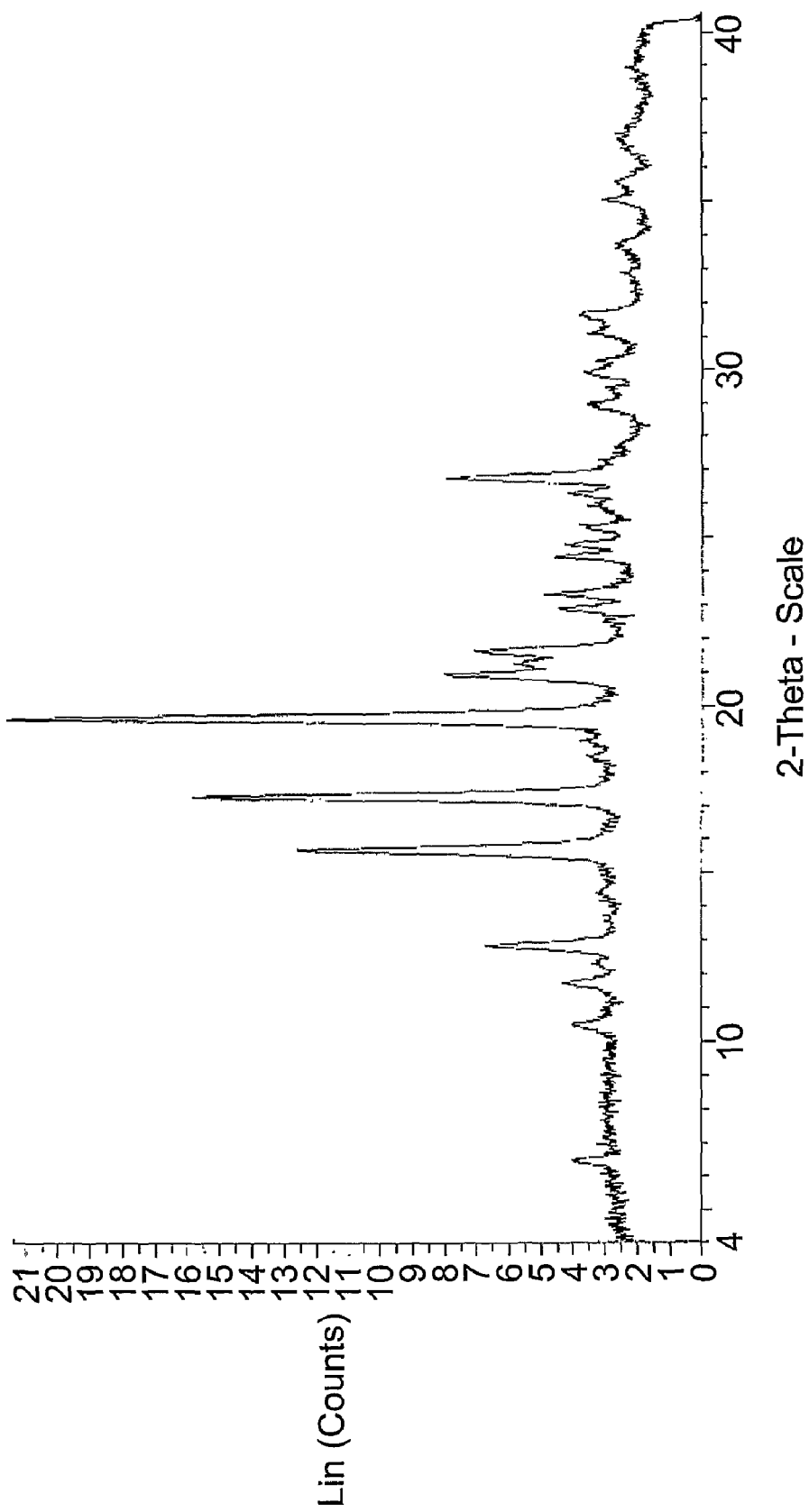
FIG. 1 shows a powder X-ray diffraction pattern of the crystalline form of free base (R)-3-[1-(2,6-dichloro-3-fluoro-phenyl)-ethoxy]-5-(1-piperidin-4-yl-1H-pyrazol-4-yl)-pyridin-2-ylamine, polymorph form 1.

A unique physical form of the free base (R)-3-[1-(2,6-dichloro-3-fluoro-phenyl)-ethoxy]-5-(1-piperidin-4-yl-1H-pyrazol-4-yl)-pyridin-2-ylamine has now been made. The powder X-ray diffraction (PXRD) pattern of free base polymorph form 1 is shown in FIG. 1, with corresponding tabulated data shown in Table 1.

TABLE 1

PXRD data tabulation for Form 1 of the free base (R)-3-[1-(2,6-dichloro-3-fluoro-phenyl)-ethoxy]-5-(1 -piperidin-4-yl-1H-pyrazol-4-yl)-pyridin-2-ylamine.

| 2θ (°) | D-Value | Peak Intensity (Counts) | Peak Intensity (%) |
|---|---|---|---|
| 12.8 | 6.916 | 6.69 | 30.9 |
| 15.7 | 5.658 | 12.6 | 58.1 |
| 17.3 | 5.129 | 15.9 | 73.3 |
| 19.7 | 4.511 | 21.6 | 100 |
| 21.0 | 4.235 | 8.00 | 37.0 |
| 21.7 | 4.102 | 7.03 | 32.5 |
| 26.8 | 3.326 | 7.92 | 36.6 |

Figure 2:
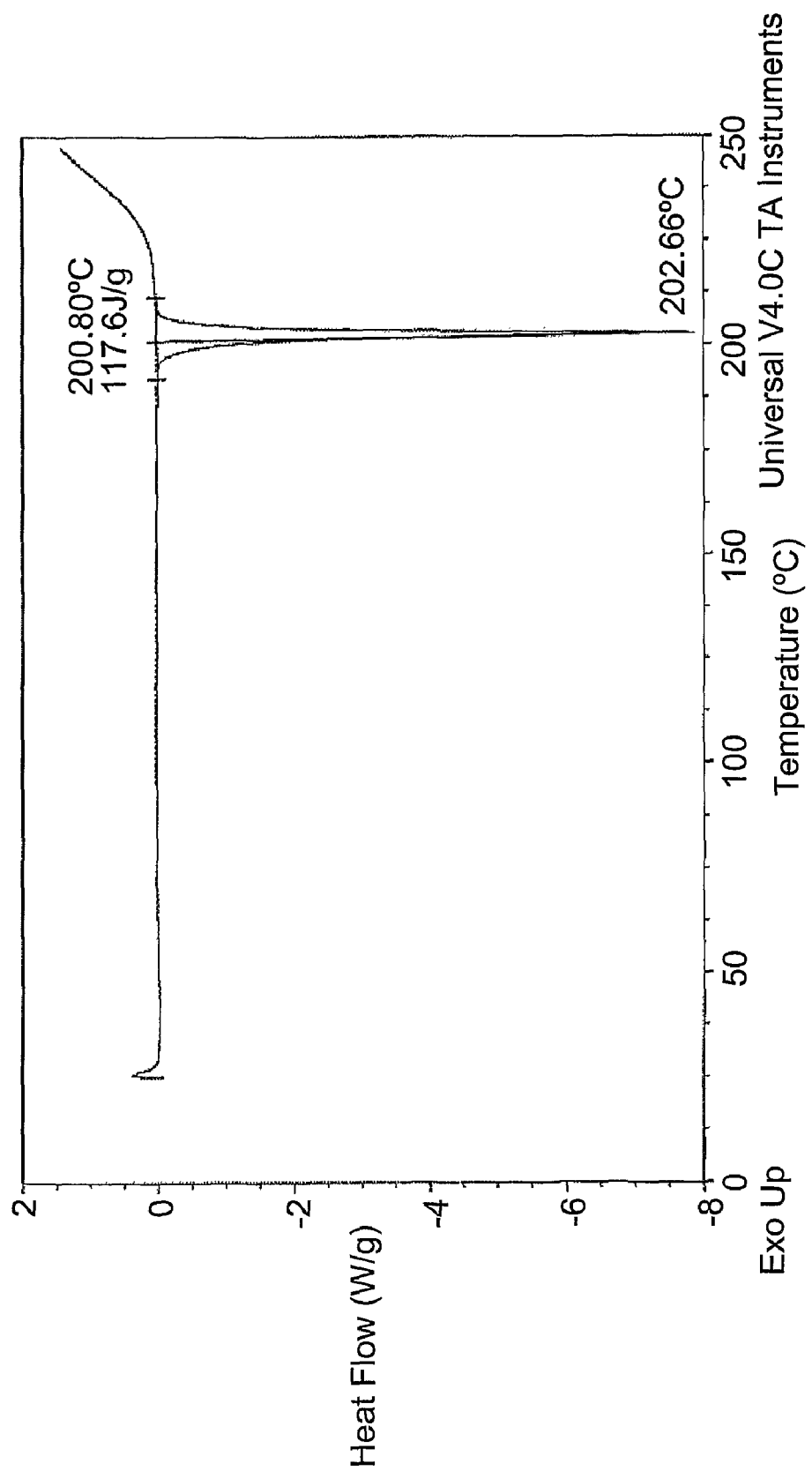
FIG. 2 shows a differential scanning calorimetery (DSC) thermogram of the crystalline form of free base (R)-3-[1-(2,6-dichloro-3-fluoro-phenyl)-ethoxy]-5-(1-piperidin-4-yl-1H-pyrazol-4-yl)-pyridin-2-ylamine, polymorph form 1.

The DSC thermogram for crystalline free base form 1 is shown in FIG. 2.

The present invention also relates to pharmaceutical compositions comprising the free base polymorph form 1 of compound 1 described herein. Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects of embodiments of the invention. It is to be understood that the scope of the present invention is not limited in any way by the scope of the following examples.

Methods and Materials

Powder X-ray Diffraction (PXRD): PXRD data shown in FIG. 1 was collected according to the following protocol. A sample (2 mg) was placed on a microscopic slide with zero background. The sample was then placed in a Discover D8 (Bruker AXS Instruments) equipped with a GADDS detector. The system used a copper X-ray source maintained at 40 kV and 40 mA to provide CUα1 emission at 1.5406 angstroms. Data were collected from 4 to 40°2θ using a step scan of 0.02° with a step time of 60.1 seconds. Diffraction peaks are typically measured with an error of ±0.1 degrees (2θ).

Differential Scanning Calorimetery (DSC): DSC measurements, shown in FIG. 2 was carried out using a Q1000, Thermal Analysis Instruments. Sample weight of 1.6 mg was placed in a hermetically sealed aluminum pan with a pinhole. The sample was equilibrated to 25° C. and then ramped to 250° C. at a scan rate of 10° C./min. Dry nitrogen was used as the purge gas.

Synthesis of Compound 1

PLE is an enzyme produced by Roche and sold through Biocatalytics Inc. as a crude esterase preparation from pig liver, commonly known as PLE-AS (purchased from Biocatalytics as ICR-123, sold as an ammonium sulfate suspension). The enzyme is classified in the CAS registry as a "carboxylic-ester hydrolase, CAS no. 9016-18-6". The corresponding enzyme classification number is EC 3.1.1.1. The enzyme is known to have broad substrate specificity towards the hydrolysis of a wide range of esters. The lipase activity is determined using a method based on hydrolysis of ethyl butyrate in a pH titrator. 1 LU (lipase unit) is the amount of enzyme which liberates 1 μmol titratable butyric acid per minute at 22° C., pH 8.2. The preparation reported herein (PLE-AS, as a suspension) is usually shipped as an opaque brown-green liquid with a declared activity of >45 LU/mg (protein content around 40 mg/mL).

(1S)-1-(2,6-dichloro-3-fluorophenyl)ethanol (1S)-1-(2,6-dichloro-3-fluorophenyl)ethanol, shown as compound (S-1) in the schemes below, was prepared by a combination of enzymatic hydrolysis of racemic 1-(2,6-dichloro-3-fluorophenyl)ethyl acetate, esterification and chemical hydrolysis with inversion according to Scheme B. Racemic 1-(2,6-dichloro-3-fluorophenyl)ethyl acetate (compound A2) was prepared according to Scheme A.

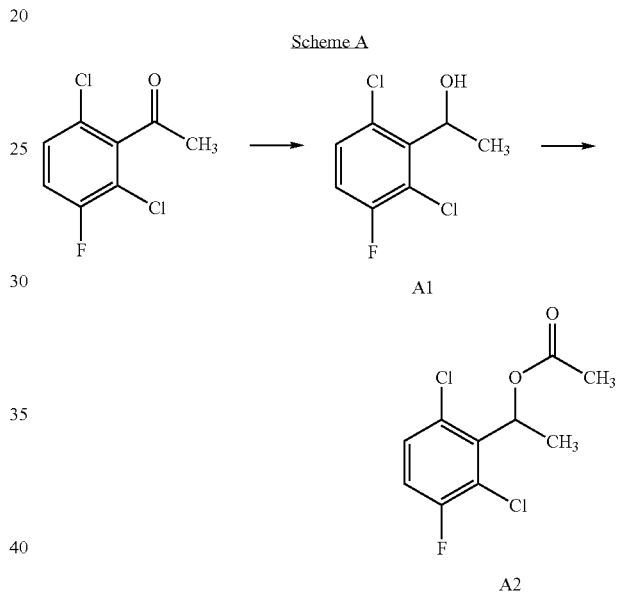

Scheme A 1-(2,6-dichloro-3-fluorophenyl)ethanol (A1): Sodium borohydride (90 mg, 2.4 mmol) was added to a solution of 2',6'-dichloro-3'-fluoro-acetophenone (Aldrich, catalog #52, 294-5) (207 mg, 1 mmol) in 2 mL of anhydrous CH₃OH. The reaction mixture was stirred at room temperature for 1 h then was evaporated to give a colorless oil residue. The residue was purified by flash chromatography (eluting with 0→10% EtOAc in hexanes) to give compound A1 as a colorless oil (180 mg; 0.88 mmol; 86.5% yield); MS (APCI) (M-H)⁻ 208; 1H NMR (400 MHz, chloroform-D) δ ppm 1.64 (d, J=6.82 Hz, 3H) 3.02 (d, J=9.85 Hz, 1H) 6.97-7.07 (m, 1H) 7.19-7.33 (m, 1H).

1-(2,6-dichloro-3-fluorophenyl)ethyl acetate (A2): Acetic anhydride (1.42 mL, 15 mmol) and pyridine (1.7 mL, 21 mmol) were added sequentially to a solution of compound A1 (2.2 g, 10.5 mmol) in 20 mL of CH₂Cl₂. The reaction mixture was stirred at room temperature for 12 h and then evaporated to give a yellowish oil residue. The residue was purified by flash chromatography (eluting with 7→9% EtOAc in hexanes) to give compound A2 as a colorless oil (2.26 g; 9.0 mmol; 85.6% yield); 1H NMR (400 MHz, chloroform-D) δ ppm 1.88 (d, J=6.82 Hz, 3 H) 2.31 (s, 3H) 6.62 (q, J=6.82 Hz, 1H) 7.25 (t, J=8.46 Hz, 1H) 7.49 (dd, J=8.84, 5.05 Hz, 1H).

Scheme B

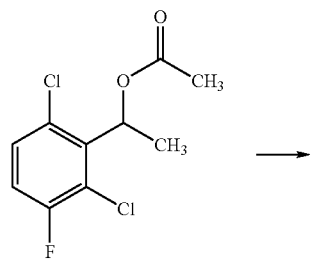

A2

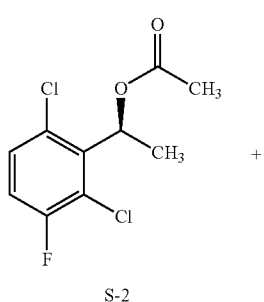

S-2

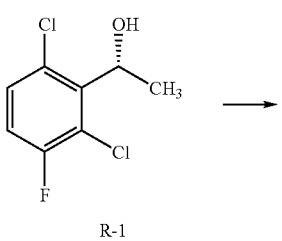

R-1

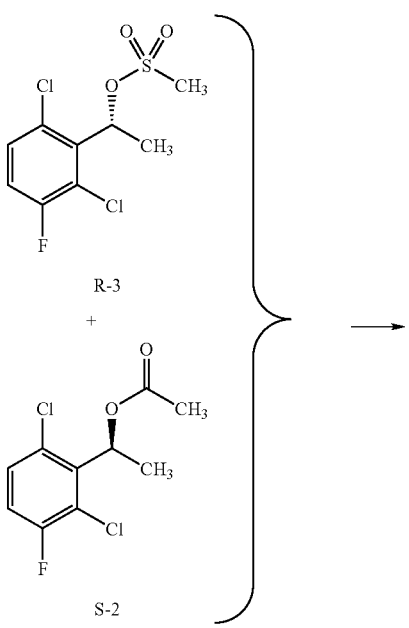

R-3
+
S-2

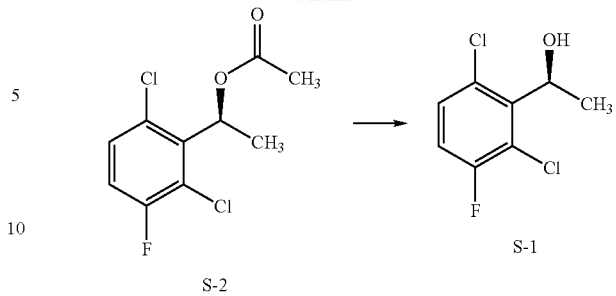

S-2

→

S-1

To a 50 mL jacketed flask equipped with a pH electrode, an overhead stirrer and a base addition line (1M NaOH), was added 1.2 mL of 100 mM potassium phosphate buffer pH 7.0 and 0.13 mL of PLE AS suspension. Then, compound A2 (0.13 g, 0.5 mmol, 1.00 eq) was added dropwise and the resulting mixture was stirred at room temperature for 20 h, maintaining the pH of the reaction constant at 7.0 using 1 M NaOH. Both the conversion and ee's of the reaction were monitored by RP-HPLC, and stopped after 50% starting material was consumed (approximately 17 hours under these conditions). The mixture was then extracted three times with 10 mL of ethyl acetate to recover both ester and alcohol as a mixture of R-1 and S-2.

Methanesulfonyl chloride (0.06 mL, 0.6 mmol) was added to a solution of a mixture of R-1 and S-2 (0.48 mmol) in 4 mL of pyridine under nitrogen atmosphere. The reaction mixture was stirred at room temperature for 3 h then evaporated to obtain an oil. Water (20 mL) was added to the mixture and then EtOAc (20 mL×2) was added to extract the aqueous solution. The organic layers were combined, dried, filtered, and evaporated to give a mixture of R-3 and S-2. This mixture was used in the next step reaction without further purification. $^1$H NMR (400 MHz, chloroform-D) δ ppm 1.66 (d, J=7.1 Hz, 3H) 1.84 (d, J=7.1 Hz, 3H) 2.09 (s, 3H) 2.92 (s, 3H) 6.39 (q, J=7.0 Hz, 1H) 6.46 (q, J=6.8 Hz, 1H) 6.98-7.07 (m, 1H) 7.07-7.17 (m, 1H) 7.23-7.30 (m, 1H) 7.34 (dd, J=8.8, 4.80 Hz, 1H).

Potassium acetate (0.027 g, 0.26 mmol) was added to a mixture of R-3 and S-2 (0.48 mmol) in 4 mL of DMF under nitrogen atmosphere. The reaction mixture was heated to 100° C. for 12 h. Water (20 mL) was added to the reaction mixture and EtOAc (20 mL×2) was added to extract the aqueous solution. The combined organic layer was dried, filtered, and evaporated to give an oil of S-2 (72 mg, 61% yield in two steps). Chirality ee: 97.6%. $^1$H NMR (400 MHz, chloroform-D) δ ppm 1.66 (d, J=7.1 Hz, 3H) 2.09 (s, 3H) 6.39 (q, J=6.8 Hz, 1H) 7.02 (t, J=8.5 Hz, 1H) 7.22-7.30 (m, 1H).

Sodium methoxide (19 mmol; 0.5 M in methanol) was added slowly to compound S-2 (4.64 g, 18.8 mmol) under a nitrogen atmosphere at 0° C. The resulting mixture was stirred at room temperature for 4 hours. The solvent was evaporated and H$_2$O (100 mL) was added. The cooled reaction mixture was neutralized with sodium acetate-acetic acid buffer solution to pH 7. Ethyl acetate (100 mL×2) was added to extract the aqueous solution. The combined organic layers were dried over Na$_2$SO$_4$, filtered, and evaporated to obtain S-1 as a white solid (4.36 g, 94.9% yield); SFC-MS: 97% ee. $^1$H NMR (400 MHz, chloroform-D) δ ppm 1.65 (d, J=6.8 Hz, 3 H) 5.58 (q, J=6.9 Hz, 1H) 6.96-7.10 (m, 1H) 7.22-7.36 (m, 1H).

5-bromo-3-[1-(2,6-dichloro-3-fluoro-phenyl)-ethoxy]-pyridin-2-ylamine (racemate)

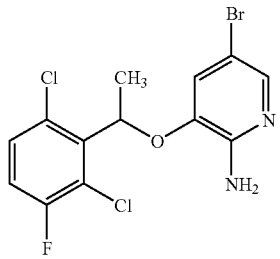

1. 2,6-Dichloro-3-fluoroacetophenone (15 g, 0.072 mol) was stirred in THF (150 mL, 0.5M) at 0° C. using an ice bath for 10 min. Lithium aluminum hydride (2.75 g, 0.072 mol) was slowly added. The reaction was stirred at ambient temperature for 3 hr. The reaction was cooled in ice bath, and water (3 mL) was added drop wisely followed by adding 15% NaOH (3 mL) slowly. The mixture was stirred at ambient temperature for 30 min. 15% NaOH (9 mL), $MgSO_4$ were added and the mixture filtered to remove solids. The solids were washed with THF (50 mL) and the filtrate was concentrated to give 1-(2,6-dichloro-3-fluoro-phenyl)-ethanol (14.8 gm, 95% yield) as a yellow oil. $^1$H NMR (400 MHz, DMSO-$d_6$) δ 1.45 (d, 3H), 5.42 (m, 2H), 7.32 (m, 1H), 7.42 (m, 1H).

2. To a stirred solution of triphenyl phosphine (8.2 g, 0.03 mol) and DEAD (13.65 mL of a 40% solution in toluene) in THF (200 mL) at 0° C. was added a solution of 1-(2,6-dichloro-3-fluoro-phenyl)-ethanol (4.55 g, 0.021 mol) and 3-hydroxy-nitropyridine (3.35 g, 0.023 mol) in THF (200 mL). The resulting bright orange solution was stirred under a nitrogen atmosphere at ambient temperature for 4 hours at which point all starting materials had been consumed. The solvent was removed, and the crude material was dry loaded onto silica gel, and eluted with ethyl acetate-hexanes (20:80) to yield 3-(2,6-dichloro-3-fluoro-benzyloxy)-2-nitro-pyridine (6.21 g, 0.021 mol, 98%) as a pink solid. $^1$H NMR ($CDCl_3$, 300 MHz) δ1.8-1.85 (d, 3H), 6.0-6.15 (q, 1H), 7.0-7.1 (t, 1H), 7.2-7.21 (d, 1H), 7.25-7.5 (m, 2H), 8.0-8.05 (d, 1H).

3. To a stirred mixture of AcOH (650 mL) and EtOH (500 mL) was suspended 3-(2,6-dichloro-3-fluoro-benzyloxy)-2-nitro-pyridine (9.43 g, 0.028 mol) and iron chips (15.7 g, 0.28 mol). The reaction was heated slowly to reflux and allowed to stir for 1 hr. The reaction was cooled to room temperature then diethyl ether (500 mL) and water (500 mL) was added. The solution was carefully neutralized by the addition of sodium carbonate. The combined organic extracts were washed with sat'd $NaHCO_3$ (2×100 mL), $H_2O$ (2×100 mL) and brine (1×100 mL) then dried ($Na_2SO_4$), filtered and concentrated to dryness under vacuum to yield 3-(2,6-dichloro-3-fluoro-benzyloxy)-pyridin-2-ylamine (9.04 g, 0.027 mol, 99%) as a light pink solid. $^1$H NMR ($CDCl_3$, 300 MHz) δ1.8-1.85 (d, 3H), 4.9-5.2 (brs, 2H), 6.7-6.84 (q, 1H), 7.0-7.1 (m, 1H), 7.2-7.3 (m, 1H), 7.6-7.7 (m, 1H).

4. A stirring solution of 3-(2,6-dichloro-3-fluoro-benzyloxy)-pyridin-2-ylamine (9.07 g, 0.03 mol) in acetonitrile was cooled to 0° C. using an ice bath. To this solution was added N-bromosuccinimide (NBS) (5.33 g, 0.03 mol) portionwise. The reaction was stirred at 0° C. for 15 min. The reaction was concentrated to dryness under vacuum. The resulting dark oil was dissolved in EtOAc (500 mL), and purified via silica gel chromatography. The solvents were then removed in vacuo to yield 5-bromo-3-(2,6-dichloro-3-fluoro-benzyloxy)-pyridin-2-ylamine (5.8 g, 0.015 mol, 51%) as a white crystalline solid. $^1$H NMR ($CDCl_3$, 300 MHz) δ1.85-1.95 (d, 3H), 4.7-5.0 (brs, 2H), 5.9-6.01 (q, 1H), 6.8-6.95 (d, 1H), 7.01-7.2 (t, 1H), 7.4-7.45 (m, 1H), 7.8-7.85 (d, 1H).

5-bromo-3-[1(R)-(2,6-dichloro-3-fluoro-phenyl)-ethoxy]-pyridin-2-ylamine

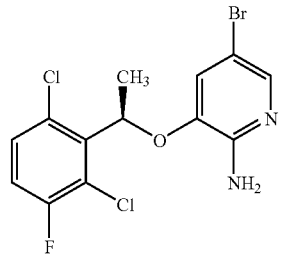

The enantiomerically pure R isomer was prepared as described above for the racemate, but using the enantiomerically pure starting materials described above. $^1$H NMR (400 MHz, DMSO-$d_6$) δ 1.74 (d, 3H), 6.40 (m, 1H), 6.52 (br s, 2H), 7.30 (m, 1H), 7.48 (m, 1H), 7.56 (s, 1H); MS m/z 382 (M+1).

4-methanesulfonyloxy-piperidine-1-carboxylic Acid Tert-butyl Ester (2)

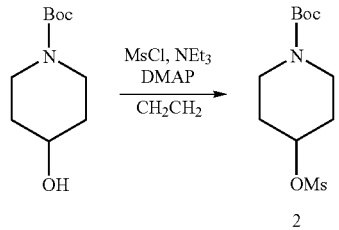

To a stirred solution of 4-hydroxy-piperidine-1-carboxylic acid tert-butyl ester (7.94 g, 39.45 mmol) in $CH_2Cl_2$ (100 mL), cooled to 0° C., was slowly added $NEt_3$ (5.54 mL, 39.45 mmol) followed by methane sulfonyl chloride (3.06 mL, 39.45 mmol) and DMAP (48 mg, 0.39 mmol). The mixture was stirred at room temperature overnight. To the mixture was added water (30 mL). Extraction with $CH_2Cl_2$ (3×30 mL) followed by drying ($Na_2SO_4$) and removal of the solvent in vacuo afforded 4-methanesulfonyloxy-piperidine-1-carboxylic acid tert-butyl ester as a white solid (11.00 g, >99% yield). $^1$H NMR ($CDCl_3$, 400 MHz) δ 4.89 (m, 1H), 3.69 (m, 2H), 3.31 (m, 2H), 3.04 (s, 3H), 1.95 (m, 2H), 1.83 (m, 2H), 1.46 (s, 9H).

tert-butyl-4-[4-(4,4,5,5-tetramethyl-1,3,2-dioxaborolan-2-yl)-1H-pyrazol-1-yl]piperidine-1-carboxylate

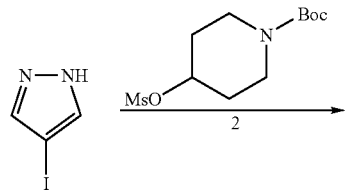

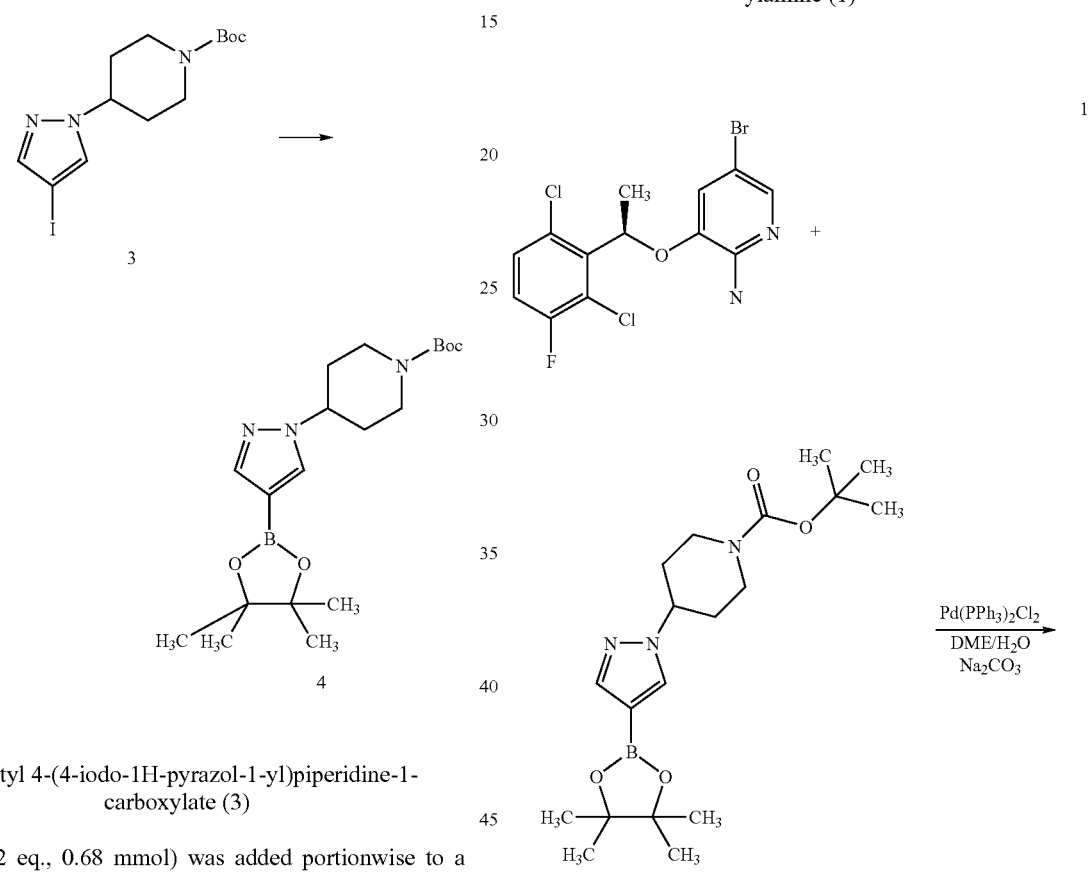

tert-butyl 4-(4-iodo-1H-pyrazol-1-yl)piperidine-1-carboxylate (3)

NaH (1.2 eq., 0.68 mmol) was added portionwise to a stirred solution of 4-iodopyrazole (0.57 mmol) in DMF (2 L) at 4° C. The resulting mixture was stirred for 1 hour at 4° C. and 4-methanesulfonyloxy-piperidine-1-carboxylic acid tert-butyl ester, compound 2 (1.1 eq., 0.63 mmol) was then added. The resulting mixture was heated to 100° C. for 12 h. The reaction was quenched with H₂O and extracted with EtOAc several times. The combined organic layers were dried, filtered, and concentrated to afford an orange oil. The residue was purified by silica gel chromatography (eluting with 5% EtOAc in pentane) to give compound 3 as a white solid (140 g, 66%).

tert-butyl-4-[4-(4,4,5,5-tetramethyl-1,3,2-dioxaborolan-2-yl)-1H-pyrazol-1-yl]piperidine-1-carboxylate (4)

Bis(pinacolato)diboron (1.4 eq., 134 g, 0.52 mol) and potassium acetate (4 eq., 145 g, 1.48 mol) were added sequentially to a solution of compound 3 (140 g, 0.37 mol) in 1.5 L of DMSO. The mixture was purged with nitrogen several times and dichlorobis(triphenylphosphino) palladium (II) (0.05 eq., 12.9 g, 0.018 mol) was then added. The resulting mixture was heated at 80° C. for 2 h. The reaction mixture was cooled to room temperature and filtered through a bed of celite and washed with EtOAc. The filtrate was washed with saturated NaCl (500 mL×2), dried over Na₂SO₄, filtered and concentrated. The residue was purified by silica gel chromatography (eluting with 5% EtOAc in hexanes) to give compound 4 as a white solid (55 g, 40%).

3-[(R)-1-(2,6-dichloro-3-fluoro-phenyl)-ethoxy]-5-(1-piperidin-4-yl-1H-pyrazol-4-yl)-pyridin-2-ylamine (1)

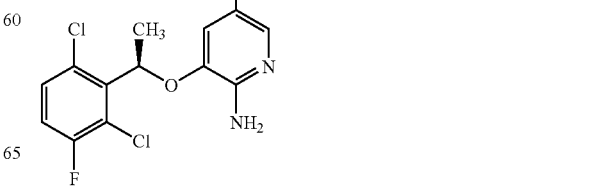

-continued

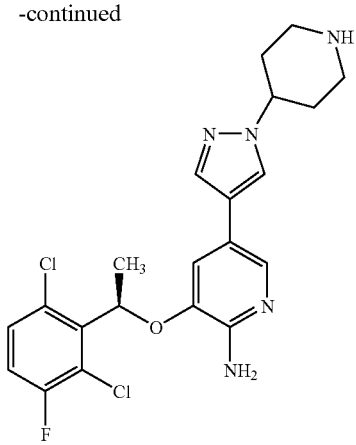

To a stirred solution of 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (15.22 g, 35.64 mmol) and 4-(4-bromo-pyrazol-1-yl)-piperidine-1-carboxylic acid tert-butyl ester (14.12 g, 42.77 mmol) in DME (143 mL) was added a solution of $Na_2CO_3$ (11.33 g, 10692 mmol) in water (36 mL). The solution was degassed and charged with nitrogen three times. To the solution was added $Pd(PPh_3)_2Cl_2$ (1.25 g, 1.782 mmol). The reaction solution was degassed and charged with nitrogen again three times. The reaction solution was stirred at 87° C. oil bath for about 16 hours (or until consumption of the borane pinacol ester), cooled to ambient temperature and diluted with EtOAc (600 mL). The reaction mixture was filtered through a pad of celite and washed with EtOAc. The EtOAc solution was washed with brine, dried over $Na_2SO_4$, and concentrated. The crude product was purified on a silica gel column eluting with EtOAc/Hexane system (Biotage 90+ Column: equilibrium 600 mL 100% Hexanes, segment 1:2250 mL 50% EtOAc/Hexanes Linear, segment 2: 4500 mL 75% EtOAc/Hexanes Linear, segment 3: 4500 mL 100% EtOAc) to afford 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (11.8 g, 60% yield, ~95% purity) with a Rf of 0.15 (50% EtOAc/Hexanes). MS m/e 550 (M+1)⁺.

To a solution of 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (11.8 g, 21.45 mmol) in $CH_2Cl_2$ (59 mL, 0.2M) was added 4N HCl/Dioxane (21 mL). The solution was stirred overnight forming a solid. The solid was crushed thoroughly with a glass rod and sonicated to release starting material trapped in the solid. Additional 4N HCl/Dioxane (21 mL) was added and stirred for another 2 hours at room temperature in which LCMS showed no starting material. The suspension was filtered in a Buchner funnel lined with filter paper. The mother liquor was saved because it contained <5% of product. The solid was transferred to a 500 mL beaker and HPLC water was added until the solid dissolved completely. The pH was adjusted to 10 with the addition of solid $Na_2CO_3$. The water solution was extracted with $CH_2Cl_2$ (5×200 mL) or until LCMS showed no product in the aqueous layer. The $CH_2Cl_2$ solution was dried over $Na_2SO_4$ and concentrated. The crude product, re-dissolved in $CH_2Cl_2$ (10 mL) and MeOH (1 mL), was purified on a silica gel column eluting with $CH_2Cl_2$/MeoH/NEt₃ system (Biotage 40+ Column: equilibrium 600 mL $CH_2Cl_2$ 100% giving byproduct, segment 1: 1200 mL 10% MeOH/$CH_2Cl_2$ linear, segment 2: 2400 mL 10% MeOH/$CH_2Cl_2$ step, segment 3: 2400 mL 9% MeOH/1% NEt₃/$CH_2Cl_2$). The desired fractions were collected to provide 3-[(R)-1-(2,6-dichloro-3-fluoro-phenyl)-ethoxy]-5-(1-piperidin-4-yl-1H-pyrazol-4-yl)-pyridin-2-ylamine (7.19 g, 75% combined yield, white solid). MS m/e 450 (M+1)⁺. ¹H NMR (DMSO-d₆, 400 MHz) δ 7.92 (s, 1H), 7.76 (s, 1H), 7.58 (m, 1H), 7.53 (s, 1H), 7.45 (m, 1H), 6.90 (s, 1H), 6.10 (m, 1H), 5.55 (bs, 2H), 4.14 (m, 1H), 3.05 (m, 2H), 2.58 (m, 2H), 1.94 (m, 2H), 1.80 (d, 3H), 1.76 (m, 2H).

The solid product 3-[(R)-1-(2,6-dichloro-3-fluoro-phenyl)-ethoxy]-5-(1-piperidin-4-yl-1H-pyrazol-4-yl)-pyridin-2-ylamine was dissolved in dichloromethane, and the solvent was evaporated slowly to generate fine crystalline solid. After high vacuum dry, the sample was confirmed to be a single crystalline polymorph form 1 with a melting point of 194° C.

The following solvents have been used for recrystallization of the solid: isopropanol, isobutanol, ethanol, ethyl acetate, toluene, tetrahydrofuran, and dioxane. All of the seven solvents generated the same polymorph form 1 crystalline solid as the original crystalline solid from dichloromethane.

We claim:

1. A crystalline form of free base of (R)-3-[1-(2,6-dichloro-3-fluoro-phenyl)ethoxy]-5-(1-piperidin-4-yl-1H-pyrazol-4-yl)-pyridin-2-ylamine having a powder X-ray diffraction pattern substantially the same as shown in FIG. 1.

2. The crystalline form of claim 1, wherein the powder X-ray diffraction pattern has a peak at diffraction angle (2θ) of 19.7±0.1.

3. The crystalline form of claim 1, wherein the powder X-ray diffraction pattern has peaks at diffraction angles (2θ) of 17.3±0.1 and 19.7±0.1.

4. The crystalline form of claim 1, wherein the powder X-ray diffraction pattern has peaks at diffraction angles (2θ) of 15.7±0.1, 17.3±0.1, and 19.7±0.1.

5. The crystalline form of claim 1, wherein the powder X-ray diffraction pattern has peaks at diffraction angles (2θ) of 15.7±0.1, 17.3±0.1, 19.7±0.1, and 26.8±0.1.

6. A pharmaceutical composition comprising the crystalline form of claim 1.

7. A capsule comprising the pharmaceutical composition of claim 6.

8. The capsule of claim 7 comprising from 0.1 to 200 mg of the crystalline form of (R)-3-[1-(2,6-dichloro-3-fluoro-phenyl)-ethoxy]-5-(1-piperidin-4-yl-1H-pyrazol-4-yl)-pyridin-2-ylamine.

9. The capsule of claim 7 comprising from 25 to 150 mg of the crystalline form of (R)-3-[1-(2,6-dichloro-3-fluoro-phenyl)-ethoxy]-5-(1-piperidin-4-yl-1H-pyrazol-4-yl)-pyridin-2-ylamine.

10. The capsule of claim 7 comprising from 50 to 100 mg of the crystalline form of (R)-3-[1-(2,6-dichloro-3-fluoro-phenyl)-ethoxy]-5-(1-piperidin-4-yl-1H-pyrazol-4-yl)-pyridin-2-ylamine.

* * * * *